United States Patent [19]  
Clack

[11] Patent Number: 4,806,912  
[45] Date of Patent: Feb. 21, 1989

[54] MONITORING SYSTEM FOR A LIQUID PURIFICATION SYSTEM

[76] Inventor: Robert A. Clack, 6409 Bridge Rd., Madison, Wis. 53713

[21] Appl. No.: 64,881

[22] Filed: Jun. 19, 1987

[51] Int. Cl.$^4$ .................... B01D 31/00; G01N 27/00
[52] U.S. Cl. ..................... 340/603; 210/85; 324/442
[58] Field of Search ............... 324/438, 439, 442, 443; 210/96.1, 96.2, 85, 746, 745; 340/603

[56] References Cited

U.S. PATENT DOCUMENTS

| | | | |
|---|---|---|---|
| 3,838,774 | 10/1974 | Dolan et al. | 210/96.2 |
| 3,990,066 | 11/1976 | Malmgren | 340/603 |
| 4,320,010 | 3/1982 | Tucci et al. | 210/96.1 |
| 4,496,906 | 1/1985 | Clack | 324/439 |
| 4,498,982 | 2/1985 | Skinner | 210/96.2 |
| 4,587,518 | 5/1986 | King | 340/603 |

Primary Examiner—Stewart J. Levy  
Assistant Examiner—Hezron E. Williams  
Attorney, Agent, or Firm—Lockwood, Alex, Fitzgibbon & Cummings

[57] ABSTRACT

A system for monitoring the operation of a water purification system of the type having an inline membrane includes a first conductivity measurement cell located upline of the membrane and a second conductivity measurement cell located downline of the membrane. The cells are electrically connected in series and across the output of a symmetrical square wave generator. A differential amplifier compares the voltage across one of the cells with a predetermined reference voltage to develop a control signal when the conductivity of downline cell relative to the upline cell rises above a predetermined threshold level. An output circuit responsive to this signal drives an appropriate one of two indicator lamps to indicate satisfactory or unsatisfactory system operation.

5 Claims, 2 Drawing Sheets

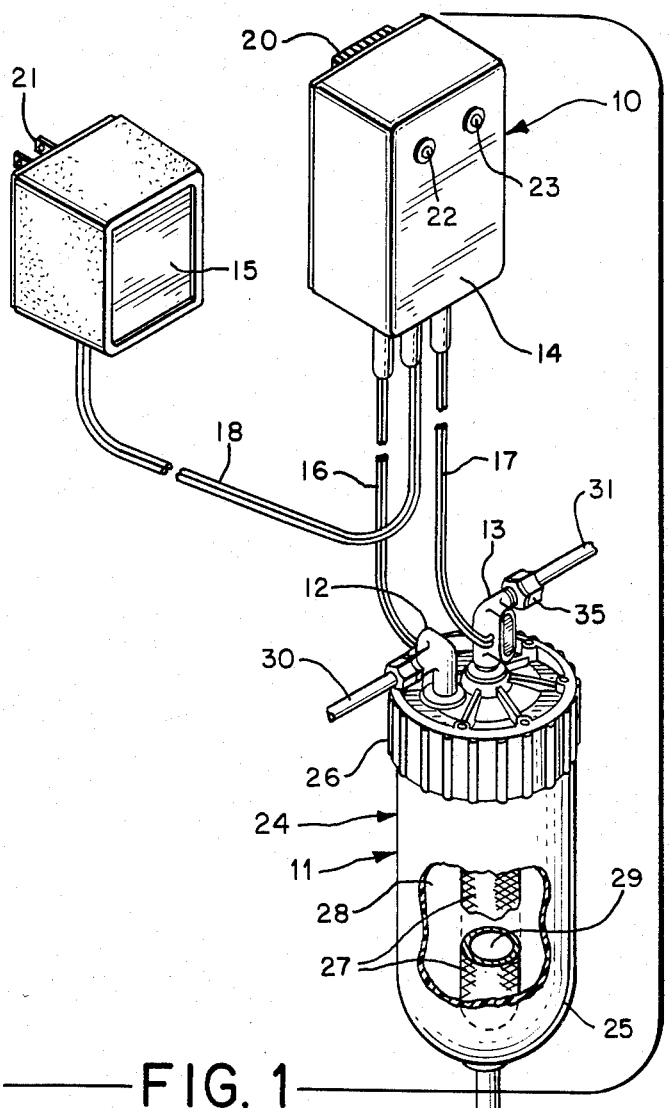
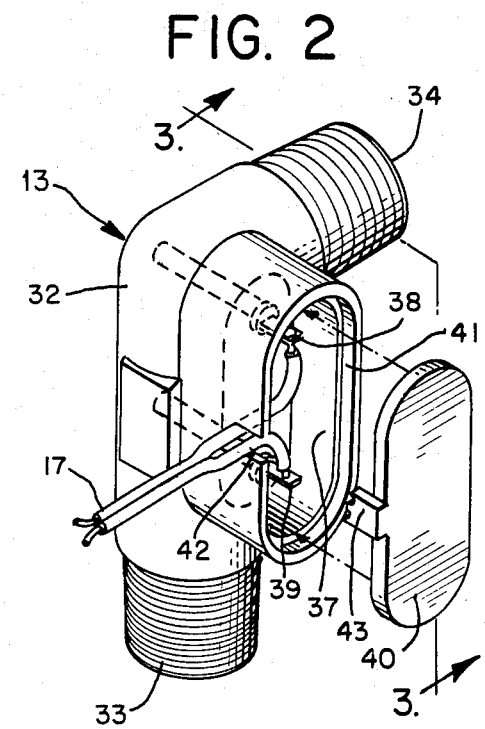
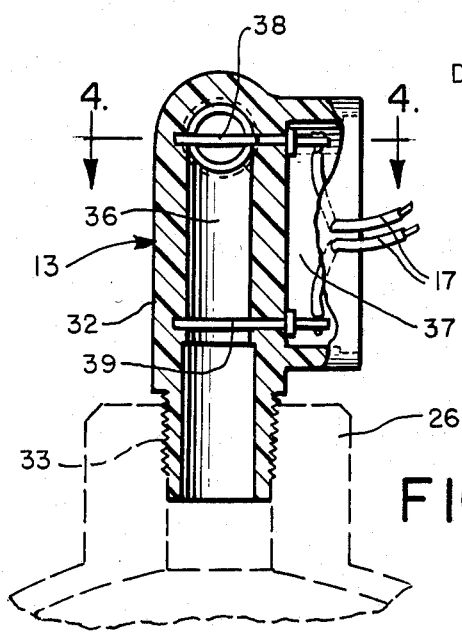
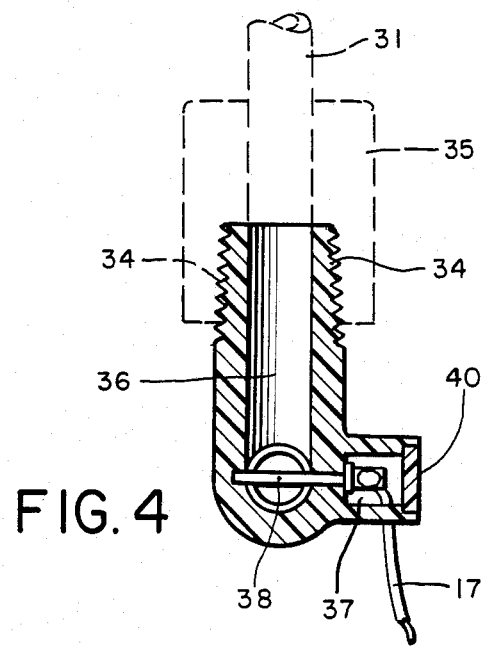
FIG. 1
FIG. 2
FIG. 3
FIG. 4

MONITORING SYSTEM FOR A LIQUID PURIFICATION SYSTEM

BACKGROUND OF THE INVENTION

The present invention is directed generally to liquid conductivity monitoring systems, and more particularly to an improved monitoring system for a reverse osmosis liquid purification system.

Reverse osmosis systems have come into wide use for removing impurities in water. In such systems, a flow of water is caused to pass through a semi-permeable membrane. Dissolved impurities, including ionic particles, are trapped by the membrane, so that water downstream of the membrane is free of the impurities and has a lower ion concentration than water upstream of the membrane.

To preclude the undetected presence of impurities in the output product, such as might occur upon rupture or deterioriation of the membrane of a reverse osmosis system, it is desirable that the system be continuously monitored and an unambiguous signal be given to the operation upon malfunction of the system. Since the conductivity of the aqueous solution undergoing purification is approximately proportional to dissolved ion concentration, which is in turn dependent on the performance of the reverse osmosis filter, an indication of system performance can be had by comparing water conductivity upstream of the filter with water conductivity downstream of the filter.

Various monitoring systems have been proposed using water conductivity including those shown in U.S. Pat. Nos. 4,587,518, 4,528,093, 4,498,982, 4,496,906 and 4,028,666. U.S. Pat. No. 4,496,906, which is a prior patent of the present inventor, in addition describes a novel two light indicator system for indicating water conductivity above or below a predetermined threshold level at a single monitoring location. The present invention is directed to an improved monitoring system for a reverse osmosis liquid processing system which is economical and reliable, and provides the user with an unambiguous indication of satisfactory system operation.

Accordingly, it is a general object of the present invention to provide a new and improved monitoring system for a liquid purification system of the type having an inline membrane.

It is a more specific object of the present invention to provide a monitoring system for a liquid purification system which is simple and reliable in construction, and which provides an unambiguous indication of unsatisfactory system operation.

SUMMARY OF THE INVENTION

The invention is directed to a monitoring system for a liquid purification system of the type having an inline membrane. The monitoring system includes a first conductivity cell comprising a first pair of electrodes disposed in the liquid at a first location upstream of the membrane and a second conductivity cell comprising a second pair of electrodes disposed in the liquid at a second location downstream of the membrane. Oscillator means provide an alternating sensing signal. The first pair of electrodes is connected in series with the second pair of electrodes, and the series-connected electrode pairs are connected across the output of the oscillator means. Amplifier circuit means responsive to the sensing signal developed across one of said electrode pairs produce a control signal indicative of the relative liquid conductivity between the cells falling below a predetermined threshold level, and output circuit means responsive to the control signal produce a user-discernible indication of malfunction of the liquid purification system.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a monitoring system constructed in accordance with the invention installed on a water purification system having an inline membrane.

FIG. 2 is a perspective view of a conductivity measurement cell constructed in accordance with the invention and installed upline and downline of the membrane in the water purification system of FIG. 1.

FIG. 3 is an enlarged cross-sectional view of the conductivity measurement cell taken along line 3—3 of FIG. 2.

FIG. 4 is a cross-sectional view of the conductivity measurement cell taken along line 4—4 of FIG. 3.

DESCRIPTION OF THE PREFERRED EMBODIMENT

Figure 5:
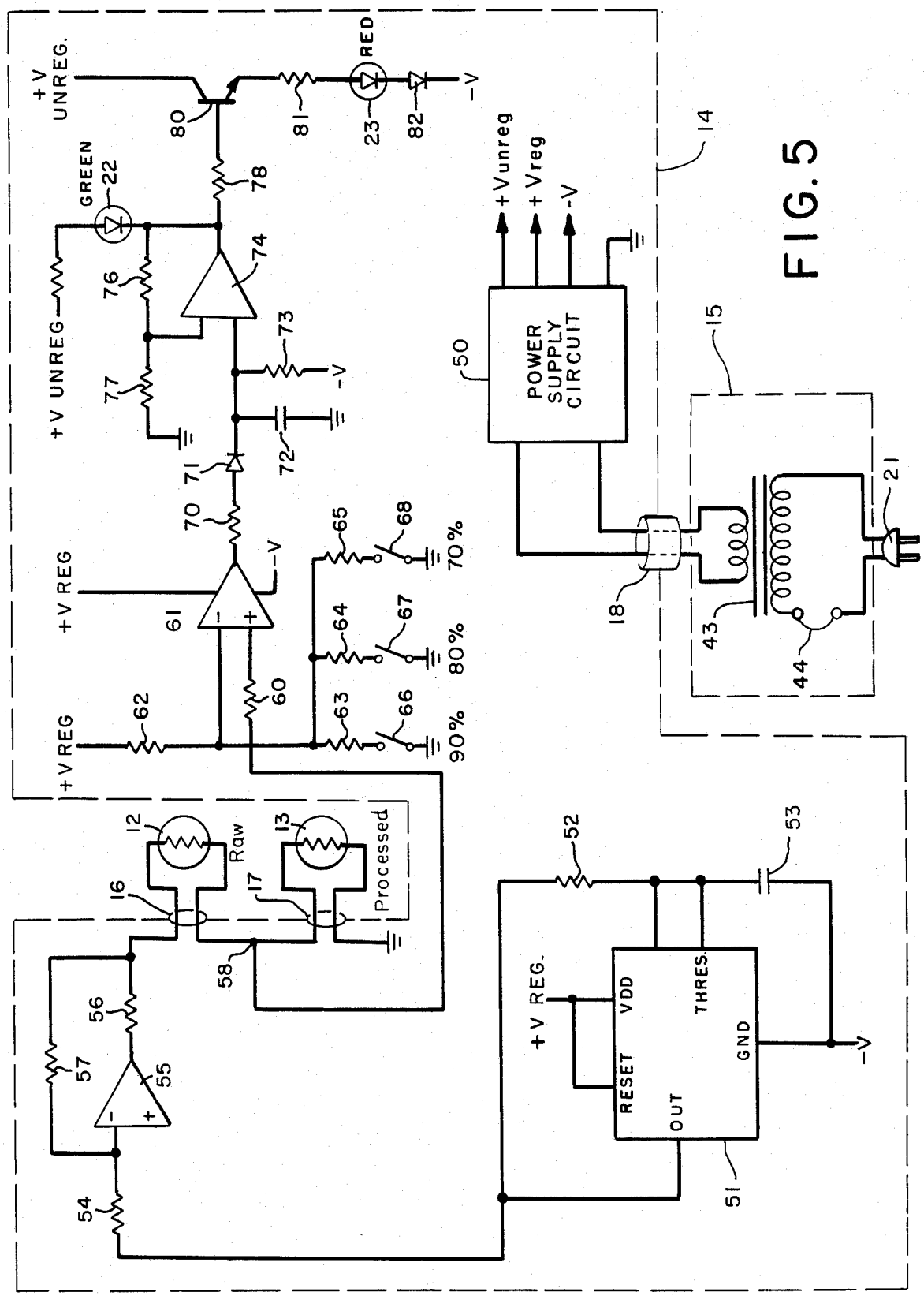
FIG. 5 is a simplified electrical schematic diagram of the monitoring system of the invention.

Referring to the Figures, and particularly to FIG. 1, a monitoring system 10 constructed in accordance with the invention for use in conjunction with a water purification construction is seen to include generally a first water conductivity measurement cell assembly 12, a second water conductivity measurement cell assembly 13, a circuit module 14 and a power supply 15. Cell assembly 12 is connected to circuit module 14 by a cable 16, cell assembly 13 is connected to circuit module 14 by a cable 17, and circuit module 14 is connected to power supply module 15 by a cable 18.

Circuit module 14 includes an integral bracket 20 of conventional construction for the purpose of mounting the module to a supporting surface (not shown). The power supply module 15 includes projecting contacts 21 for insertion into a standard AC electrical receptacle.

Satisfactory operation of the water purification system 11 is indicated by a green light emitting diode (LED) 22 on the front panel of circuit module 14. Unsatisfactory operation is indicated by an amber LED 23 on the same surface. In operation, either the green LED 22 is lit, signifying satisfactory operation, or the amber LED 23 is lit, signifying unsatisfactory operation. In addition, as will be developed, external devices such as remote indicator lamps, relays and/or buzzers may be provided if required.

A single filter assembly 24 is shown as part of water purification system 11, which may be entirely conventional in construction and operation. The filter 24 assembly, which is also of conventional construction, includes a generally cylindrical housing 25 having a hemispheric closed bottom end and an open top end over which a cap assembly 26 is threadedly engaged.

Within housing 25, depending from the cap assembly 26, a generally cylindrical membrane assembly 27 of conventional construction separates the interior of the housing into a peripheral upline chamber 28 and a central downline chamber 29.

Unpurified water is admitted to the upline chamber 28 through an inlet conduit 30 and purified water is removed from the downline chamber 29 through an outlet conduit 31. It will be understood that the reverse osmosis system 11 may include in addition to membrane assembly 24 a pump, a filter and one or more valve assemblies. Such additional elements are well known to the art and consequently are not shown here, reference being made to the previously identified prior art patents and other reference material for a description of such conventional systems.

The inlet conduit 30 is connected to upline chamber 28 by cell assembly 12, which advantageously takes the general form of a right angle connector. Similarly, tubing segment 31 is connected to downline chamber 29 by cell assembly 13, which also takes the general form of a right angle connector and may be identical to cell assembly 12.

Referring to FIG. 2, cell assembly 13 is seen to comprise a housing 32 having a threaded portion 33 at one end for engaging an appropriate port of cap assembly 26, and a second threaded portion 34 at its other end, arranged at right angles to threaded portion 33, for engaging a threaded collar assembly 35 (FIG. 1) associated with tubing segment 31.

As best shown in FIGS. 3 and 4, housing 32 defines an interior fluid passageway 36 which extends the length of the housing, forming a right angle between the end portions to provide for fluid flow between the ports of cap assembly 26 and conduit segments 30 and 31.

Also included in housing 32 is a chamber 37 for receiving connecting cable 17. Within chamber 37 the individual conductors of cable 17 connect with respective electrodes 38 and 39 which project from chamber 37 through the connecting wall of housing 32 into fluid passageway 36. The electrodes 38 and 39 are spaced apart within fluid passageway 36 such that electrical conduction path will occur between the electrodes in the presence of fluid in passageway 36. The resistance of the electrical connection thus provided between the electrodes is a function of the conductivity of the liquid in the passageway, and cell assembly 13 provides this information to circuit module 14 through the interconnecting cable 17. Since housing 32 is constructed of a non-conductive material such as a plastic or epoxy, the electrodes 38 and 39 are effectively electrically insulated from each other except for the conductivity provided by fluid in passageway 36.

Chamber 37 also provides a convenient location for soldering the individual wires of cable 17 to the exposed ends of the electrodes. Once the connections have been made, a cover 40 can be pressed into a complimentarily dimensioned recess 41 in housing 32 to close chamber 37. A notch 42 provides for passage of cable 17 into chamber 37 and a projection 43 on the edge of cover 40 secures the cable in position.

Thus, the cell assembly 13 provides a compact and cost-efficient means for sensing fluid conductivity. By reason of its unique construction, the sensing electrodes 38 and 39 are securely and accurately positioned within fluid passageway 36 during the molding of housing 32, while at the same time a mechanically and electrically protective chamber 37 is formed over the ends of the electrodes. Connections are conveniently made to the electrodes by conventional soldering techniques and an interlocking cap 40 simultaneously encloses the soldered connections and anchors the cable.

Referring to FIG. 5, power supply module 15 is seen to include a transformer 43 having a primary winding connected to the AC plug assembly 21 through a conventional fuse 44. The secondary winding of transformer 43 is connected through cable 18 to a conventional power supply circuit 50 within circuit module 14. In a conventional manner, circuit 50 develops $+V$ unregulated, $+V$ regulated and $-V$ voltages for powering the monitoring system.

Within module 14 a symmetrical square wave signal is developed by a multivibrator 51 and associated circuitry which includes a frequency determining network comprising a resistor 52 and a capacitor 53. The multivibrator 51 provides a symmetrical square wave signal at a frequency of approximately 200 hertz. This signal is supplied through a resistor 54 to the inverting input of a first operational amplifier 55, which serves as a buffer amplifier to condition the square wave signal for application to cell assemblies 12 and 13. To this end, the non-inverting input of the amplifier is grounded and a series output resistor 56 is provided in combination with a degenerative feedback resistor 57.

In accordance with the invention, cell assemblies 12 and 13 are connected in series to receive the conditioned output signal from buffer amplifier 55. In particular, output resistor 56 is connected to one electrode of cell assembly 12, the remaining electrode of this cell assembly is connected to one electrode of cell assembly 13, and the remaining terminal of which is connected to a plane reference potential, in this case electrical ground. With the square wave thus applied to the electrodes, plating of the electrodes as would occur from application of a direct current voltage is avoided.

The two serially connected cell assemblies act as a voltage divider with respect to the applied square wave signal from amplifier 55. As a result, the portion of the applied signal present at the commonly connected electrodes of the two cell assemblies, juncture 58, depends on the conductivity of the downline cell 13 relative to conductivity of the upline cell 12. In particular, when the downline conductivity is relatively less, the signal at juncture 58 is relatively more, signifying satisfactory operation of purification system 11. Conversely, when the conductivity of cell 13 is greater, and less disparity exists between the conductivity of the two cells, the signal appearing at juncture 58 is relatively lower, signifying unsatisfactory operation of the processing system.

To provide an unambiguous indication to the user of system status juncture 58 s connected through a resistor 60 to the non-inverting input of a second operational amplifier 61. The inverting input of amplifier 61 is connected to a source of reference potential provided by a voltage divider consisting of a resistor 62 connected to the regulated output of power supply circuit 50, and one of three resistors 63-65 selected for inclusion in the voltage divider by respective switches 66-68. In practice, the selection is made either during manufacture of the monitoring system or during installation by the user to establish a threshold level above which the signal at juncture 58 will cause amplifier 61 to provide an output.

The resistance of resistor 63 may be selected to provide in conjunction with resistor 62 a reference voltage level which will be exceeded when the conductivity experienced by cell 13 exceeds that provided by a 90% effective membrane. Similarly, resistor 64 may be selected to provide upon closure of switch 67 an output from amplifier 61 upon the membrane efficiency falling below 80%, and resistor 65 may be selected so that upon closure of switch 68 an output is produced by amplifier 61 upon the membrane efficiency falling below 70%.

The output of amplifier 61 is applied through a resistor 70 to a rectifier circuit comprising a diode 71, capacitor 72 and resistor 73 selected to develop from the 200 hertz amplified output from amplifier 61 a DC control voltage indicative of the threshold level designated by the selected one of resistors 63-65 being exceeded. This control voltage is applied to the non-inverting input of a third operational amplifier 74 which serves as a driver for the green and amber indicator lights 22 and 23. To this end, the output of amplifier 74 is connected to the unregulated +V output of power supply circuit 50 through the green LED 22 and a resistor 75. A degenerative feedback circuit is provided by a resistor 76 connected between the output of the amplifier and the inverting input of the amplifier, and a second resistor 77 connected between the inverting input and ground.

A second output resistor 78 is connected to an LED driver transistor 80. The collector of transistor 80 is connected to the +V unregulated output of power supply circuit 50 and the emitter of the transistor is connected through a resistor 81, the amber LED 23 and a diode 82 to the −V output of the supply circuit.

With this output arrangement, in the absence of an output from amplifier 74, as when no signal is applied to the non-inverting input of the amplifier, the output of the amplifier is logic low and the green LED 22 is caused to light by reason of current flow through resistor 75 and the amplifier. Conversely, when the output of amplifier 74 is logic high, as in the presence of an enabling signal on the non-inverting input, the green LED 22 is extinguished and transistor 80 is biased into conduction, causing the red LED 23 to receive current through the transistor, resistor 81 and diode 82. Diode 82 is provided in series with LED 23 to prevent the application of excessive voltage to the LED.

Thus, in operation when membrane 27 is functioning properly to provide the degree of purification called for by the selected one of resistors 63-65, the differential signal developed at juncture 58 is sufficient to overcome the reference voltage applied to the inverting input of amplifier 61 and that device is inhibited. Consequently, a control signal is developed by the signal detecting circuit for application to amplifier 74, and that amplifier provides a logic low output which causes the green LED 22 to be lit. However, when membrane 27 is not performing to the selected threshold level, the signal at juncture 58 is less than that applied to the inverting input of amplifier 61 and an output is produced by the amplifier. This output is rectified by diode 71, capacitor 72 and resistor 73 to develop a control voltage at the non-inverting input of amplifier 74, which conditions that amplifier to a logic high output state. This causes the green LED 22 to be extinguished and transistor 80 to be driven into saturation, causing the red LED 23 to light.

Where desired, a bell or buzzer of conventional construction can be substituted for resistor 81 to provide an aural warning of system malfunction at either a local or remote location.

By reason of the novel series-connection between cell assemblies 12 and 13 circuit complexity is greatly reduced for improved reliability and reduced cost of construction. Furthermore, by reason of the novel mechanical construction of the cell assemblies, the system can be readily installed on existing purification systems without modification of the systems. The novel right-angle design of the cell assembly housings and provision for connection to the integral electrodes and anchoring of the connecting cables by means of an integral chamber in the housing further enhances the installation.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A monitoring system for a liquid purification system of the type having an inline membrane, comprising:
    a first conductivity cell comprising first and second electrodes disposed in spaced relationship in the liquid at a first location upstream of the membrane;
    a second conductivity cell comprising third and fourth electrodes disposed in spaced relationship in the liquid at a second location downstream of the membrane;
    oscillator means having a pair of output terminals and providing across said terminals a symmetrical AC signal, one of said output terminals being connected to ground;
    said second electrode being connected to said third electrode, and said first electrode and said fourth electrode being connected to respective ones of said output terminals, whereby said first and second conductivity cells are connected in series across the output of said oscillator means;
    amplifier circuit means having first and second input terminals, one of said input terminals being connected to said second and third electrodes, and the other of said input terminals being connected to a reference potential relative to ground, for developing an output signal indicative of the difference between liquid conductivities in said first and second conductivity cells; and
    output circuit means responsive to said amplifier output signal for producing a user-discernible indication of said conductivity difference exceeding a predetermined threshold level.

2. A monitoring system for a liquid purification system as defined in claim 1 wherein said amplifier circuit means comprise a differential amplifier, one of the input terminals of said differential amplifier being connected to said interconnected second and third electrodes, and the other of the input terminals of said differential amplifier being connected to a source of predetermined reference potential, and wherein said reference potential is variable over a predetermined range to establish said predetermined threshold level.

3. A monitoring system for a liquid purification system as defined in claim 1 wherein the non-inverting input terminal of said differential amplifier is connected to said second and third electrodes and the inverting input terminal of said differential amplifier is connected to said source of reference potential.

4. A monitoring system for a liquid purification system as defined in claim 1 wherein said output circuit means include indicator means, rectifier means for developing a control signal indicative of the amplitude of said amplifier output signal, and differential amplifier means for amplifying said control signal to drive said indicator means.

5. A monitoring system for a liquid purification system as defined in claim 4 wherein said indicator means comprise a first light indicating unsatisfactory system performance, and a second light indicating satisfactory performance, and said first light is powered only when said differential in conductivity exceeds said predetermined threshold level, and said second light is powered only when said differential in conductivity does not exceed said predetermined threshold level.

* * * * *